(12) United States Patent
Hayes et al.

(10) Patent No.: US 7,528,264 B2
(45) Date of Patent: May 5, 2009

(54) HYDRIDE REDUCTION PROCESS FOR PREPARING QUINOLONE INTERMEDIATES

(75) Inventors: Michael Patrick Hayes, Plymouth, NY (US); Tammy Talbot Schunk, Unadilla, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 119 days.

(21) Appl. No.: 11/728,341

(22) Filed: Mar. 26, 2007

(65) Prior Publication Data

US 2007/0232806 A1 Oct. 4, 2007

Related U.S. Application Data

(60) Provisional application No. 60/786,450, filed on Mar. 28, 2006.

(51) Int. Cl.
*C07D 207/28* (2006.01)
*C07D 295/00* (2006.01)

(52) U.S. Cl. .................. 548/534; 548/400; 548/530; 548/531; 548/532; 548/533

(58) Field of Classification Search ................ 548/400, 548/530, 531, 532, 533, 534
See application file for complete search history.

(56) References Cited

U.S. PATENT DOCUMENTS

| | | | |
|---|---|---|---|
| 4,017,622 A | 4/1977 | Minami et al. |
| 4,341,784 A | 7/1982 | Matsumoto et al. |
| 4,448,962 A | 5/1984 | Irikura et al. |
| 4,544,658 A | 10/1985 | Petersen et al. |
| 4,544,747 A | 10/1985 | Ishikawa et al. |
| 4,665,079 A | 5/1987 | Culbertson et al. |
| 4,771,054 A | 9/1988 | Domagala et al. |
| 4,780,468 A | 10/1988 | Bridges et al. |
| 4,822,801 A | 4/1989 | Domagala et al. |
| 4,855,292 A | 8/1989 | Ueda et al. |
| 4,894,458 A | 1/1990 | Masuzawa et al. |
| 4,920,120 A | 4/1990 | Domagala et al. |
| 4,988,709 A | 1/1991 | Ogata et al. |
| 4,997,943 A | 3/1991 | Iwata et al. |
| 5,043,450 A | 8/1991 | Masuzawa et al. |
| 5,051,509 A | 9/1991 | Nagano et al. |
| 5,098,912 A | 3/1992 | Hayakawa et al. |
| 5,116,834 A | 5/1992 | Domagala et al. |
| 5,281,612 A | 1/1994 | Domagala et al. |
| 5,286,723 A | 2/1994 | Hayakawa et al. |
| 5,348,961 A | 9/1994 | Iwata et al. |
| 5,364,861 A | 11/1994 | Hagen et al. |
| 5,457,104 A | 10/1995 | Bartel et al. |
| 5,519,016 A | 5/1996 | Kimura et al. |
| 5,547,962 A | 8/1996 | Ito et al. |
| 5,556,979 A | 9/1996 | Philipps |
| 5,563,155 A | 10/1996 | Domagala et al. |
| 5,648,567 A | 7/1997 | Marhold et al. |
| 5,770,597 A | 6/1998 | Kim et al. |
| 6,329,391 B1 | 12/2001 | Ledoussal et al. |
| 6,387,928 B1 | 5/2002 | Ledoussal et al. |
| 6,803,469 B2 | 10/2004 | Randall |
| 6,849,740 B2 | 2/2005 | Ledoussal et al. |
| 7,019,143 B2 | 3/2006 | Ledoussal et al. |
| 2002/0049192 A1 | 4/2002 | Ledoussal et al. |
| 2002/0173501 A1 | 11/2002 | Ledoussal et al. |
| 2003/0207862 A1 | 11/2003 | Ledoussal et al. |
| 2005/0101589 A1 | 5/2005 | Ledoussal et al. |
| 2006/0100436 A1 | 5/2006 | Ledoussal et al. |

FOREIGN PATENT DOCUMENTS

| | | |
|---|---|---|
| CA | 2217164 | 10/1996 |
| CA | 2228536 | 8/1998 |
| EP | 207497 A2 | 1/1987 |
| EP | 230295 A2 | 7/1987 |
| EP | 235762 A1 | 9/1987 |
| EP | 237955 | 9/1987 |
| EP | 443498 A1 | 8/1991 |
| EP | 550016 A1 | 7/1993 |
| EP | 0 641 793 A1 | 3/1995 |
| IT | 1279532 | 1/1997 |
| JP | 51-086476 | 7/1976 |
| JP | 01-056673 | 8/1987 |
| JP | 62-255482 | 11/1987 |
| JP | 64-016767 | 1/1989 |
| JP | 97244733 | 8/1991 |
| JP | 05-345777 | 12/1993 |
| JP | 8133977 | 5/1996 |
| JP | 09-052893 A | 2/1997 |

(Continued)

OTHER PUBLICATIONS

Bastin, Richard J., et al., "Salt Selection and Optimisation Procedures for Pharmaceutical New Chemical Entities," Organic Process Research & Development, 2000, vol. 4, pp. 427-435.

(Continued)

*Primary Examiner*—Kamal A Saeed
*Assistant Examiner*—Samantha L Shterengarts
(74) *Attorney, Agent, or Firm*—Angela M. Stone; Andrew A. Paul

(57) ABSTRACT

Hydride process for making acyclic diol intermediates from cyclic intermediates, useful in antibacterial quinolone synthesis.

20 Claims, No Drawings

FOREIGN PATENT DOCUMENTS

| JP | 10-287669 | 4/1997 |
| JP | 09-136886 | 5/1997 |
| JP | 97178847 | 6/1997 |
| JP | 97240318 | 8/1997 |
| WO | WO 97/19072 A1 | 5/1997 |
| WO | WO 97/29102 | 8/1997 |
| WO | WO 99/14214 A1 | 3/1999 |
| WO | WO 2004/014893 A | 2/2004 |
| WO | WO 2005/033108 A | 4/2005 |

OTHER PUBLICATIONS

Albrecht, "Development of Antibacterial Agents of the Nalidixic Acid Type," Prog. In Drug Research, 21 (1977) pp. 9-104.

Berge, M., et al., "Pharmaceutical Salts," Journal of Pharmaceutical Sciences, Jan. 1977, vol. 66, No. 1, pp. 1-19.

Bouzard, et al., "Fluoronaphthyridines and Quinolones as Antibacterial Agents, 1. Synthesis and Structure-Activity Relationships of New 1-Substituted Derivatives", J.Med. Chem., 32 (1989), pp. 537-42/.

Brena-Valle, Leonardo Jr., et al.,, "Synthesis of a new chiral amine: (S)-5, 5-dimethyl-2-methoxymethyl-pyrrolidine," Synthetic Communications, 31(5) 2001, pp. 697-706.

Cecchetti, V., et al., "Potent 6-Desfluoro-8-methylquinolones as New Lead Compounds in Antibacterial Chemotherapy," J. Med. Chem., vol. 39, pp. 4952-4957 (1996).

Cecchetti, et al., "Studies on 6-Aminoquinolones: Synthesis and Antibacterial Evaluation of 6-Amino-8-methylquinolones", J. Med. Chem., 39 (1996) pp. 4952-4957.

Chemical Abstracts 96: 47559 1981 Otsuka.

Chemical Abstracts 120: 298485, 1993, Ito.

Chemical Abstracts 126: 157539, 1994, Abstract by Bartel.

Chemical Abstracts 130: 223178, 1999, Tojima.

Chemical Abstracts 130: 124998, 1999, Yamamoto.

Chemical Abstracts 129: 343410, 1998, Takemura.

Chemical Abstracts 129: 153244, 1998, Sawa.

Cornett, et al., "Chap. 14. Quinolone Antibacterial Agents", Annual Reports in Medicinal Chemistry, 1985, pp. 145-154.

Coudert, Elisabeth et al., "A convenient and efficient synthesis of (2S, 4R)- and (2S, 4S)-4-methylglutamic acid," Synthesis, (8) pp. 863-865, 1997.

Domagala et al., "7-Substituted 5-Amino-1 cyclopropyl-6,8-difluoro- 1,4-dihyro-4oxo3-quinolinecarboxylic Acids: Synthesis and Biological Activity of a New Class of Quinolone Antibacterials", J. Med. Chem., 31 (1988), pp. 503-506.

Domagala et al., "Quinolone Antibacterials Containing the New 7-[3-(1-Aminoethyl)-1 pyrrolidinyl] Side Chain: The Effects of the 1-Aminoethyl Moiety and its Stereochemical Configurations on Potency and in Vivo Efficacy", J. Med. Chem. 36 (1993) pp. 871-882.

Domagala et al., "1-Substituted 7-[3-Ethylamino)methyl]-1 pyrrolidinyl]-6,8-difluoro-1, 4-dihydro-4-oxo-3-quinoline carboxylic Acids. New Quantitive Structure-Activity Relationship at N 1 for the Quinolone Antibacterials", J. Med. Chem., 31 (1988), pp. 991-1001.

Fernandes et al., "Chap. 12 Quinolones", Annual Reports in Medicinal Chemistry, 1987, pp. 117-126.

Hagen, et al., "Synthesis and Antibacterial Activity on New Quinolones Containing a 7-[3-(Amino-1, methylethyl)-1-pyrrolidinyl] Moiety. Gram-Positive Agents with Excellent Oral Activity and Low Side-Effect potential", J. Med. Chem. 37 (1994), pp. 733-738.

Hanessian, Stephen, et al., "1,3-Asymmetric Induction in Dianionic Allylation Reactions of Amino Acid Derivatives-Synthesis of Functionally Useful Enantiopure Glutamates, Pipecolates and Pyroglutamates, " Tetrahedron Letters 39 (1998) pp. 5887-5890.

Hayashi et al., "A Novel des-F(6)-Quinolone: Synthesis In Vitro Activity of 7-(Isoindoline-5-yl) Derivatives", Abstracts in New Antimicrobials, 1997, p. 173; Poster Presentation.

Hong, et al., "Novel 5-Amino-6-methylquinolone Antibacterials: A New Class on Non-6-Fluoroquinolones", Bioorganic & Medicinal Chem. Letters, 7 (1997) pp. 1875-1878.

Klopman, et al., "Computer Automated Structure Evaluation of Uinolone Antibacterial Agents", Antimicrob. Agents Chemother., 31 (1987), pp. 1831-1840.

Koga, et al., "Structure-Activity Relationships of Antibacterial 6,7- and 7,8-Disubstitued 1-Alkyl-1,4-dihydro-4-oxoquinoline-3carboxylic Acids," J. Med. Chem., 23 (1980), pp. 1358-1363.

Ledoussal, et al., "Potent Non-6-Fluoro-Substituted Quinolone Antibacterials: Synthesis and Biological Activity", J. Med. Chem., 35 (1992), pp. 198-200.

Marpat 121: 31574, Lerchen, 1996.

Marpat 121: 57343, Kimura, 1993.

Marpat: 119: 56157, Nimura, 1993.

Marpat 111: 153779, Chiba, 1989.

Rodriguez-Spong, B., et al., "General Principles of Pharmaceutical Solid Polymorphism: A Supramolecular Perspective," Science Direct, Advanced Drug Delivery Reviews 56 (2004) pp. 241-274.

Rosen et al., "Asymmetric Synthesis and Properties of the Enantimoers of the Anitbacterial Agent 7-(3-Aminopyrrolidin-1-yl)-1-(2,4-difluroophenyl)-1,4-dihydro-6-fluoro-4-oxo-1,8-naphthyridine-3-carboxylic Acid Hydrochloride", J. Med. Chem., 31 (1988), pp. 1580-1590.

Rosen et al., "Desing, Synthesis, and Properties of (4S) -7-4(Amino-2substituted-pyrrolidin 1-yl) quinolone-3-carboxylic Acids", J. Med Chem., 31 (1988), pp. 1596-1622.

Sanchez, et al., "Quinolone Antibacterial Agents, Synthesis and Structure-Activity Relationships of 8-Substituted Quinoline-3-carboxylic Acids and 1,8 Naphthyridine-3-carboxylic Acids", J. Med. Chem., 31 (1988); pp. 983-991.

Tabarrini, Oriana et al., "6-Hydroxy Derivative as New Desluoroquinolone (DFQ): Synthesis and DNA-Binding Study", Nucleosides, Nucleotides & Nucleic Acids, vol. 19(8), 2000, pp. 1327-1336.

Wentland, et al., "Chap. 15. Quinolone Antibacterial Agents", Annual Reports in Medicinal Chemistry, 1985, pp. 145-154.

Wolfson et al., "The Fluoroquinolones: Structures, Mechanisms of Action and Resistance, and Specra of Activity In Vitro", Antimicrob. Agents Chemother., 28 (1985), pp. 581-586.

Xiam et al., "Synthesis and In Vitro Antibacterial Activity of Some 1-(Diluoromethoxphenyl) quinolone-3-carboxylic Acids", J. Pharm. Sciences. 78 (1989), pp. 585-588.

U.S. Appl. No. 10/085,786, filed Feb. 28, 2002, Ledoussal, et al.

U.S. Appl. No. 11/301,685, filed Dec. 13, 2005, Ledoussal, et al.

U.S. Appl. No. 11/728,343, Mar. 26, 2007, Redman-Furey et al.

U.S. Appl. No. 11/728,342, Mar. 26, 2007, Michael Reilly.

HYDRIDE REDUCTION PROCESS FOR PREPARING QUINOLONE INTERMEDIATES

CROSS REFERENCE TO RELATED APPLICATIONS

This application claims the benefit of U.S. Provisional Application No. 60/786,450, filed on Mar. 28, 2006.

FIELD OF THE INVENTION

The present invention relates to preparation of certain quinolone intermediates, more particularly, to a direct hydride process for making acyclic diol intermediates from cyclic intermediates.

BACKGROUND OF THE INVENTION

Synthesis of various quinolone compounds have been reported in the literature, e.g., U.S. Pat. No. 6,329,391; U.S. Pat. No. 6,803,469; B. Ledoussal et al., "Non 6-Fluoro Substituted Quinolone Antibacterials: Structure and Activity", *J. Med. Chem.*, Vol. 35, p. 198-200 (1992); V. Cecchetti et al., "Studies on 6-Aminoquinolines: Synthesis and Antibacterial Evaluation of 6-Amino-8-methylquinolones", *J. Med. Chem.*, Vol. 39, pp. 436-445 (1996); V. Cecchetti et al., "Potent 6-Desfluoro-8-methylquinolones as New Lead Compounds in Antibacterial Chemotherapy", *J. Med. Chem.*, Vol. 39, pp. 4952-4957 (1996)).

The quinolone compounds (3S,5S)-7-[3-amino-5-methyl-piperidinyl]-1-cyclopropyl-1,4-dihydro-8-methoxy-4-oxo-3-quinolinecarboxylic acid, and (3S,5R)-7-[3-amino-5-methyl-piperidinyl]-1-cyclopropyl-1,4-dihydro-8-methoxy-4-oxo-3-quinolinecarboxylic acid are disclosed in the U.S. Pat. No. 6,329,391, which is herein incorporated by reference in its entirety. However, there is a need in the art for improved methods for preparing these and like antimicrobial compounds.

SUMMARY OF THE INVENTION

The present invention relates to a process of hydride reduction to prepare intermediates useful in antibacterial quinolone synthesis.

In one embodiment, the invention relates to preparing a quinolone intermediate having the formula:

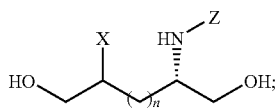

Formula (I)

wherein, n is 1 or 2; X is selected from the group consisting of $C_1$-$C_4$ alkyl, $C_6$-$C_{10}$ aryl or alkylaryl, and $C_3$-$C_6$ cycloalkyl; and Z is selected from the group consisting of $CO_2X$ and COX, wherein X is as defined above;
said process comprising the step of reacting the compound of Formula (II):

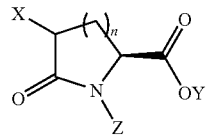

Formula (II)

wherein Y is selected from the group consisting of $C_1$-$C_4$ alkyl, $C_6$-$C_{10}$ aryl or alkylaryl, and $C_3$-$C_6$ cycloalkyl; and X, Z, and n are as defined for Formula (I); in an admixture of $C_1$-$C_4$ alkanol/$C_2$-$C_6$ ether in a ratio (v/v) of from about 100/0 to about 20/80, at about −20° C. to about 10° C., and about 2 to about 4 equivalents of sodium borohydride; followed by addition of about 1.5 to about 3.0 equivalents of a calcium salt at about 5° C. to about 15° C.

In another embodiment of the above-described process, X is $C_1$-$C_4$ alkyl.

In another embodiment of the above-described process, X is methyl.

In another embodiment of the above-described process, X is tert-butyl.

In another embodiment of the above-described process, Z is tert-butoxycarbonyl.

In another embodiment of the above-described process, the calcium salt is calcium chloride.

In another embodiment of the above-described process, the compound of Formula (II) is (2S,4S)-1-(1,1-dimethylethyl)-4-methyl-5-oxo-1,2-pyrrolidinedicarboxylic acid-2-methyl ester.

In another embodiment of the above-described process, the compound of Formula (II) is (2S,4R)-1-(1,1-dimethylethyl)-4-methyl-5-oxo-1,2-pyrrolidinedicarboxylic acid-2-methyl ester.

In another embodiment of the above-described process, the compound of Formula (I) is (1S,3S)-(4-Hydroxyl-1-hydroxymethyl-3-methyl-butyl)-carbamic acid tert-butyl ester:

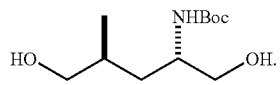

In another embodiment of the above-described process, the compound of Formula (I) is (1S,3R)-(4-Hydroxyl-1-hydroxymethyl-3-methyl-butyl)-carbamic acid tert-butyl ester:

HO_____OH with NHBoc

In another embodiment of the above-described process, the alkanol solvent is ethanol.

In another embodiment of the above-described process, the ether solvent is methyl tert-butyl ether.

In another embodiment of the above-described process, the solvent ratio (v/v) of ethanol:methyl tert-butyl ether is 33:67.

DETAILED DESCRIPTION OF THE INVENTION

The protecting groups used for nitrogen include, but are not limited to, acyl groups such as an acetyl, phenylacetyl, and formyl; carbamate groups such a tert-butoxycarbonyl or tert-amyloxycarbonyl.

The protecting groups for the carboxyl group include, but are not limited to, $C_1$-$C_4$ alkyl groups such as methyl, ethyl, n-propyl, isopropyl, and n-butyl; aryl groups such as phenyl, naphthyl; aryl-alkyl groups such as benzyl, diphenylmethyl.

The compound of the general formula (I) may be produced by subjecting a compound of the general formula (II) to a hydride reduction reaction.

Formula (I)

Formula (II)

For the compounds of Formulae (I) and (II), n is 1 or 2; X is selected from the group consisting of $C_1$-$C_4$ alkyl, $C_6$-$C_{10}$ aryl or alkylaryl, and $C_3$-$C_6$ cycloalkyl; Z is selected from the group consisting of $CO_2X$ and COX, wherein X is as defined above; and Y is selected from the group consisting of $C_1$-$C_4$ alkyl, $C_6$-$C_{10}$ aryl or alkylaryl, and $C_3$-$C_6$ cycloalkyl.

In one embodiment, the compound of Formula (I) is (1S, 3S)-(4-Hydroxyl-1-hydroxymethyl-3-methyl-butyl)-carbamic acid tert-butyl ester:

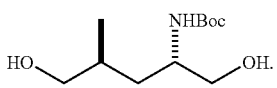

In another embodiment, the compound of Formula (I) is (1S,3R)-(4-Hydroxyl-1-hydroxymethyl-3-methyl-butyl)-carbamic acid tert-butyl ester:

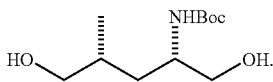

In one embodiment, the compound of Formula (II) is (2S, 4S)-1-(1,1-dimethylethyl)-4-methyl-5-oxo-1,2-pyrrolidinedicarboxylic acid-2-methyl ester:

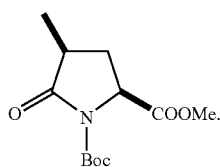

In another embodiment, the compound of Formula (II) is (2S,4R)-1-(1,1-dimethylethyl)-4-methyl-5-oxo-1,2-pyrrolidinedicarboxylic acid-2-methyl ester:

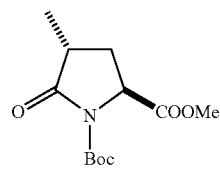

The solvents which may be used in this reaction are an alkanol, preferably a $C_1$ to $C_4$ alkanol, or and admixture of an alkanol and an ether, preferably a $C_2$ to $C_6$ ether. Preferred alkanols include but are not limited to: methanol, ethanol, propanol, isopropanol, and butanol. Preferred ethers include but are not limited to: methyl tert-butyl ether (MTBE), ethylene glycol dimethyl ether, diethyl ether, tetrahydrofuran, diisopropyl ether, and dioxane. These solvents may be used in admixture at varying ratios.

In one embodiment, the ratio of the admixture of alkanol: ether is from about 100:0 to about 20:80 (v/v).

In one embodiment the ratio of alkanol:ether is 33:67 (v/v).

A reducing agent that may be used for the reaction is sodium borohydride, in combination with a calcium salt suitable to participate in the reduction, preferably via interaction with the reducing agent. A factor to consider in determining the suitability of the calcium salt is its solubility. Unsuitable calcium salts are those which are too insoluble in the reaction solvent to effectively participate in the reduction. Suitable calcium salts include, but are not limited to, calcium chloride and calcium bromide.

In one embodiment, the calcium salt that may be used is calcium chloride.

Compound II, solvents, and about 2 to 4 equivalents of sodium borohydride may be mixed at about −20° C. to about 10° C., followed by addition of about 1.5 to about 3.0 equivalents of a calcium salt at about 5° C. to about 15° C. Where the mixing step is conducted at temperatures below those described, a phenomenon may be observed where the reaction "sleeps", resulting in the build up a reagents, such that when the reaction is sufficiently warmed, an undesirable degree of exothermic (which may even be characterized as "violent") reaction may occur. This may pose significant risks for safety in large-scale manufacturing. Adding calcium salt within the described temperature range is believed to help control the exothermic properties of the reaction. Where the mixing step is conducted at temperatures above those described, the resulting compounds may exhibit inferior, perhaps unsuitable for pharmaceutical use, purity, particularly with regard to isomeric purity.

The reaction may be carried out in about 10 mL to 100 mL of solvent per one gram of reactant.

The completion of the reaction may be monitored by known techniques, including, but not limited to, HPLC, TLC, and IR.

EXAMPLES

Example 1

Synthesis of (3S,5S)-7-[3-amino-5-methyl-piperidinyl]-1-cyclopropyl-1,4-dihydro-8-methoxy-4-oxo-3-quinolinecarboxylic acid and Malate Salt Thereof A. Synthesis of (3S,5S)-(5-Methyl-piperidin-3-yl)-carbamic acid tert-butyl ester (8):

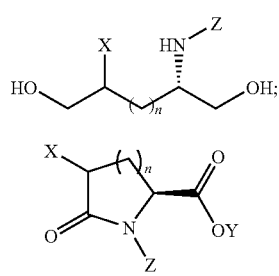

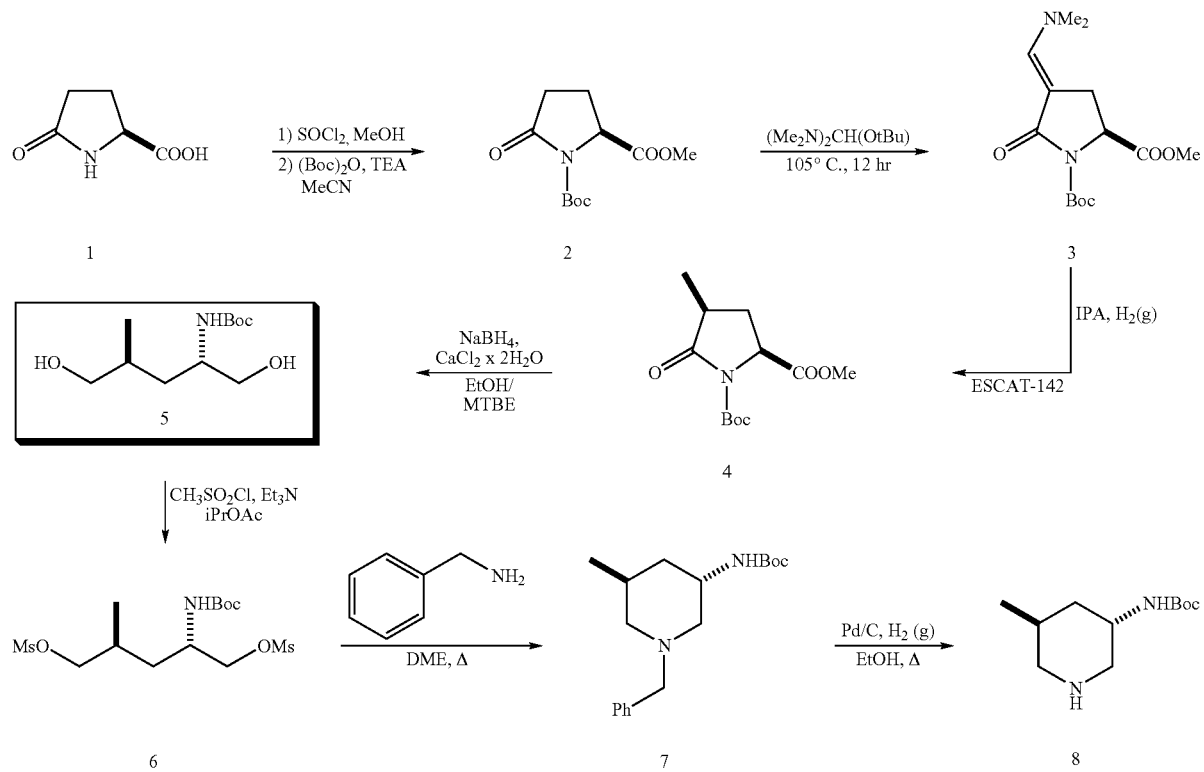

(2S)-1-(1,1-Dimethylethyl)-5-oxo-1,2-pyrrolidinedicarboxylic acid-2-methyl ester, (2). A 50-L reactor is charged with compound (1) (5.50 Kg, 42.60 mol), methanol (27 L) and cooled to 10-15° C. Thionyl chloride (10.11 Kg, 2.0 equiv.) is added via addition funnel over a period of 65 min, with external cooling to maintain temperature at <30°. The resulting solution is stirred at 25° C.±5° C. for 1.0 hour, after which the methanol is distilled off under reduced pressure. The resulting thick oil is azeotroped with ethyl acetate (3×2.5 L) to remove residual methanol. The residue is dissolved in ethyl acetate (27.4 L), charged into a 50 L reactor, and neutralized by the addition of triethylamine (3.6 Kg) from an addition funnel over 30 minutes. The temperature of the neutralization is maintained below 30° C. via external cooling. The resulting suspension of triethylamine hydrochloride is removed by filtration, and the clarified mother liquor solution is charged to a 50 L reactor, along with DMAP (0.53 Kg). Di-tert-butyl dicarbonate (8.43 Kg) is added via hot water heated addition funnel, over a period of 30 min with external cooling to maintain temperature at about 20-30° C. The reaction is complete after 1 hour as determined by TLC analysis. The organic phase is washed with ice cold 1N HCl (2×7.5 L), saturated sodium bicarbonate solution (1×7.5 L), and dried over magnesium sulfate. The mixture is filtered through a nutsche filter and ethyl acetate is removed under reduced pressure to yield a crystalline slurry that is triturated with MTBE (10.0 L) and filtered to afford intermediate (2) as a white solid (5.45 Kg, 52.4%). Anal. Calcd for $C_{11}H_{17}NO_5$: C, 54.3; H, 7.04; N, 5.76. Found: C, 54.5; H, 6.96; N, 5.80. HRMS (ESI+) Expected for $C_{11}H_{18}NO_5$, [M+H] 244.1185. Found 244.1174; $^1$H NMR (CDCl$_3$, 500 MHz): δ=4.54 (dd, J=3.1, 9.5 Hz, 1H), 3.7 (s, 3H), 2.58-2.50 (m, 1H), 2.41 (ddd, 1H, J=17.6, 9.5, 3.7), 2.30-2.23 (m, 1H), 1.98-1.93 (m, 1H), 1.40 (s, 9H); $^{13}$C NMR (CDCl$_3$, 125.70 MHz) δ 173.3, 171.9, 149.2, 83.5, 58.8, 52.5, 31.1, 27.9, 21.5; Mp 70.2° C.

(2S,4E)-1-(1,1-Dimethylethyl)-4-[(dimethylamino)methylene]-5-oxo-1,2-pyrrolidinedicarboxylic acid-2-methyl ester (3). A 50-L reactor is charged with intermediate (2) (7.25 Kg, 28.8 mol), DME (6.31 Kg), and Bredereck's Reagent (7.7 Kg, 44.2 mole). The solution is agitated and heated to 75° C.±5° C. for at least three hours. The progress of the reaction is monitored by HPLC. The reaction is cooled to 0° C.±5° C. over one hour during which time a precipitate forms. The mixture is held at 0° C.±5° C. for one hour and filtered though a nutsche filter and the product dried in a vacuum oven for at least 30 hours at 30° C.±5° C. to give intermediate (3) as a white crystalline solid (6.93 Kg, 77.9%). Anal. Calcd for $C_{14}H_{22}N_2O_5$: C, 56.4; H, 7.43; N, 9.39. Found C, 56.4; H, 7.32; N, 9.48; HRMS (ESI+) Expected for $C_{14}H_{22}N_2O_5$, [M+H] 299.1607. Found 299.1613; $^1$H NMR (CDCl$_3$, 499.8 MHz) δ=7.11 (s, 1H), 4.54 (dd, 1H, J=10.8, 3.6), 3.74 (s, 3H), 3.28-3.19 (m,1H), 3.00 (s, 6H), 2.97-2.85 (m, 1H), 1.48 (s, 9H); $^{13}$C NMR (CDCl$_3$, 125.7 MHz) δ=172.6, 169.5, 150.5, 146.5, 90.8, 82.2, 56.0, 52.3, 42.0, 28.1, 26.3. Mp 127.9° C.

(2S,4S)-1-(1,1-Dimethylethyl)-4-methyl-5-oxo-1,2-pyrrolidinedicarboxylic acid-2-methyl ester (4). A 10-gallon Pfaudler reactor is inerted with nitrogen and charged with ESCAT 142 5% palladium powder on carbon (50% wet, 0.58 Kg wet wt.), intermediate (3) (1.89 Kg, 6.33 mol) and isopropanol (22.4 Kg). The reaction mixture is agitated under a 45-psi hydrogen atmosphere at 45° C. for 18 hrs. The reaction mixture is then cooled to room temperature and filtered though a bed of Celite (0.51 Kg) in a nutsche filter to remove catalyst. The mother liquor is evaporated under reduced pressure to give a thick oil that crystallizes on standing to afford 4

(1.69 Kg, 100%) as a 93:7 diastereomeric mixture. A sample of product mixture is purified by preparative HPLC to give material for analytical data. Anal. Calcd for $C_{12}H_{19}NO_5$: C, 56.0; H, 7.44; N, 5.44. Found C, 55.8; H, 7.31; N, 5.44; MS (ESI$^+$) Expected for $C_{12}H_{19}NO_5$, [M+H] 258.1342. Found 258.1321; $^1$H NMR (CDCl$_3$, 499.8 MHz) δ=4.44 (m, 1H), 3.72 (s, 3H), 2.60-2.48 (m, 2H), 1.59-1.54 (m, 1H), 1.43 (s, 9H), 1.20 (d, j=6.8 Hz,3H); $^{13}$C NMR (CDCl$_3$, 125.7 MHz) δ=175.7, 172.1, 149.5, 83.6, 57.4, 52.5, 37.5, 29.8, 27.9, 16.2. Mp 89.9° C.

(1S,3S)-(4-Hydroxyl-1-hydroxymethyl-3-methyl-butyl)-carbamic acid tert-butyl ester (5). A 50-L reactor is charged with intermediate (4) (3.02 Kg, 11.7 mol), absolute ethanol (8.22 Kg), and MTBE (14.81 Kg). The solution is agitated and cooled to 0° C.±5° C. and sodium borohydride (1.36 Kg, 35.9 mol) is added in small portions so as to maintain reaction temperature at 0° C.±5° C. A small amount of effervescence is observed. The reaction mixture is warmed to 10° C.±5° C. and calcium chloride dihydrate (2.65 Kg,) is added portion wise at a slow rate over an hour so as to maintain a reaction temperature of 10° C.±5° C. The reaction is allowed to warm to 20° C.±5° C. over one hour and agitated for an additional 12 hours at 20° C.±5° C. The reaction is cooled to −5° C.±5° C., ice-cold 2N HCl (26.9 Kg) is added at a rate to maintain a reaction temperature of 0° C.±5° C. Agitation is stopped to allow phases to separate. The lower aqueous phase (pH=1) is removed. The reactor is charged with aqueous saturated sodium bicarbonate (15.6 Kg) over five minutes. Agitation is stopped to allow phases to separate. The lower aqueous phase (pH=8) is removed. The reactor is charged with magnesium sulfate (2.5 Kg) and agitated for at least 10 minutes. The mixture is filtered though a nutsche filter, and condensed under reduced pressure to afford intermediate (5) (1.80 Kg, 66%). Anal. Calcd for $C_{11}H_{23}NO_4$: C, 56.6H, 9.94; N, 6.00. Found C, 56.0; H, 9.68; N, 5.96; HRMS (ESI$^+$) Expected for $C_{11}H_{24}NO_4$, [M+H] 234.1705. Found 234.1703; $^1$H NMR (CDCl$_3$, 500 MHz) δ=6.34 (d, J=8.9 Hz, 1H, NH), 4.51 (t, J=5.8, 5.3 Hz, 1H, NHCHCH$_2$OH), 4.34 (t, J=5.3, 5.3 Hz, 1H, CH3CHCH$_2$OH), 3.46-3.45, (m, 1H, NHCH), 3.28 (dd, J=10.6, 5.3 Hz, NHCHCHHOH), 3.21 (dd, J=10.2, 5.8 Hz, 1H, CH$_3$CHCHHOH), 3.16 (dd, J=10.2, 6.2 Hz, 1H, NHCHCHHOH), 3.12 (dd, J=10.6, 7.1 Hz, 1H, CH$_3$CHCH HOH), 1.53-1.50 (m, 1H, CH$_3$CHCHHOH), 1.35 (s, 9H, O(C H$_3$)$_3$, 1.30 (ddd, J=13.9, 10.2, 3.7 Hz, 1H, NHCHCHHCH), 1.14 (ddd, J=13.6, 10.2, 3.4 Hz, 1H, NHCHCHHCH), 0.80 (d, J=6.6 Hz, 3H, CH$_3$); $^{13}$C NMR (CDCl$_3$, 125.7 MHz) δ 156.1, 77.9, 50.8, 65.1, 67.6, 65.1, 35.6, 32.8, 29.0, 17.1. Mp 92.1° C.

(2S,4S)-Methanesulfonic acid 2-tert-butoxycarbony-lamino-5-methanesulfonyloxy-4-methyl-pentyl ester (6). A 50 L reactor is charged with a solution of intermediate (5) (5.1 Kg) in isopropyl acetate (i-PrOAc) (11.8 Kg) followed by a rinse with an additional 7.9 Kg i-PrOAc. The reaction is cooled to 15° C.±5° C. and triethylamine (TEA) (7.8 Kg) is added while maintaining the set temperature. The reactor is further cooled to 0° C.±5° C. and methanesulfonyl chloride (MsCl) (6.6 Kg) is added to the reaction solution while maintaining the set temperature. The reaction is stirred for a few hours and monitored for completion by HPLC or TLC. The reaction is quenched by the addition of a saturated aqueous bicarbonate solution and the resulting isolated organic phase is washed successively with cold 10% aqueous triethylamine solution, cold aqueous HCl solution, cold saturated aqueous bicarbonate solution, and finally saturated aqueous brine solution. The organic phase is dried, filtered, and concentrated in vacuo below 55° C.±5° C. until a solid/liquid slurry containing intermediate (6) is obtained. The slurry is used crude in subsequent reaction without further characterization.

(3S,5S)-(1-Benzyl-5-methyl-piperidin-3-yl)-carbamic acid tert-butyl ester (7). A 50 L reactor is charged with 9.1 Kg of neat benzylamine. The reactor is brought to 55° C. and a solution of intermediate (6) (8.2 Kg) in 1,2-dimethoxyethane (DME) (14.1 Kg) is added to the reactor while maintaining a temperature of 60° C.±5° C. After complete addition of this solution, the reaction is stirred at 60° C.±5° C. for several hours and monitored for completion by TLC or HPLC. The reaction is cooled to ambient temperature and volatiles (DME) are removed by rotary evaporation under vacuum. The residue is diluted with 11.7 Kg of 15% (v/v) ethyl acetate/hexanes solution and treated, while agitating, with 18.7 Kg of 20% (wt) aqueous potassium carbonate solution. A triphasic mixture is obtained upon settling. The bottom aqueous phase is removed and the middle phase is set aside. The upper organic phase is collected and held for combination with extracts from additional extractions. The isolated middle phase is extracted twice again with 11.7 Kg portions of 15% (v/v) ethyl acetate/hexanes solution, each time combining the extracts with original organic phase. The combined organic extracts are transferred into a rotary evaporator and solvent is removed under vacuum until an oily residue remains. The residue is then purified via large-scale preparative chromatography to afford purified intermediate (7) as an oil.

(3S,5S)-(5-Methyl-piperidin-3-yl)-carbamic acid tert-butyl ester (8). A 40 L pressure vessel is charged with 0.6 Kg 50% wet, solid palladium on carbon (E101, 10 wt. %) under flow of nitrogen. A solution of 3.2 Kg intermediate (7) in 13.7 Kg of absolute ethanol is then charged to the reactor under nitrogen. The reactor is purged with nitrogen and is then pressurized with hydrogen at 45 psi. The reaction is then heated to 45° C. while maintaining a hydrogen pressure of 45 psi. The reaction is monitored by TLC or LC until complete. The reaction is cooled to ambient temperature, vented, and purged with nitrogen. The reactor contents are filtered through a bed of Celite and the solids are washed with 2.8 Kg of absolute ethanol. The filtrate is concentrated by rotary evaporation under vacuum until a waxy solid is obtained to afford intermediate (8): TLC R$_f$ (Silica F$_{254}$, 70:30 v/v ethyl acetate-hexanes, KMnO$_4$ stain)=0.12; $^1$H NMR (300 MHz, CDCl$_3$) δ 5.31 (br s, 1H), 3.80-3.68 (m, 1H), 2.92 (d, J=11.4 Hz, 1H), 2.77 (AB quart, J$_{AB}$=12.0 Hz, Δv=50.2 Hz, 2H), 2.19 (t, J=10.7 Hz, 1H), 1.82-1.68 (m, 2H), 1.54 (br s, 1H), 1.43 (s, 9H), 1.25-1.15 (m, 1H), 0.83 (d, J=6.6 Hz,3H); $^{13}$C NMR (75 MHz, CDCl$_3$) δ 155.3, 78.9, 54.3, 50.8, 45.3, 37.9, 28.4, 27.1, 19.2; MS (ESI+) m/z 215 (M+H), 429 (2M+H).

B. Synthesis of 1-Cyclopropyl-7-fluoro-8-methoxy-4-oxo-1,4-dihydro-quinoline-3-carboxylic acid (19):
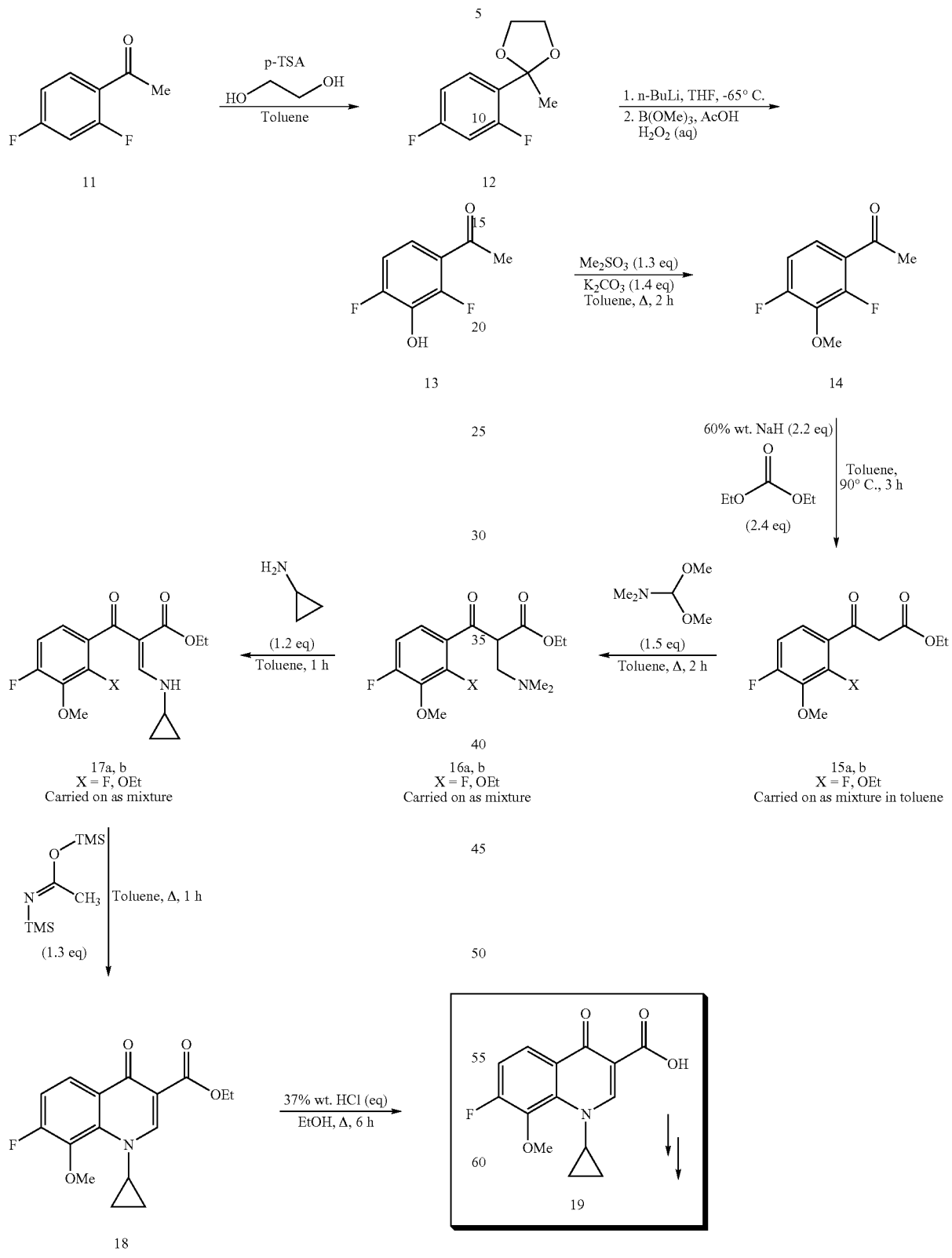
68% overall from 13

Intermediate (12): A reactor is charged with a solution of intermediate (11) (1.2 Kg, 7.7 mol, 1.0 eq) in anhydrous toluene (12 L) followed by ethylene glycol (1.8 L, 15.7 mol, 4.2 eq) and solid p-toluenesulfonic acid (120 g, 10 wt. %). The reaction mixture is stirred at ambient temperature for at least 30 minutes and then heated to reflux, collecting the water/toluene azeotrope in a Dean Stark type trap apparatus until the reaction is complete as determined by TLC analysis (15% EtOAc/Hexanes v/v). Upon completion, the reaction is cooled to ambient temperature and poured into an aqueous solution of sodium bicarbonate (6 L). The organic toluene phase was removed and washed with saturated sodium bicarbonate solution (6 L), distilled water (2×6 L), and saturated aqueous brine (6 L). The organic phase was removed and dried over $MgSO_4$, filtered, and evaporated under reduced pressure to afford intermediate (12) as an oil (1.3 Kg, 86%). The material is used without further purification in subsequent reaction steps.

Intermediate (13): A reactor is charged with a solution of intermediate (12) (1.2 Kg, 6.0 mol, 1.0 eq) in anhydrous tetrahydrofuran (12 L) and n-butyllithium (2.5M in hexanes, 2.6 L, 6.6 mol, 1.1 eq) is added at −40° C., while maintaining this temperature throughout the addition. The reaction is stirred for at least one hour at −40° C. and trimethylborate (0.9 L, 7.8 mol, 1.3 eq) is added to the mixture while maintaining the temperature at or below −40° C. The reaction mixture is stirred for at least one hour at −40° C. until complete as determined by TLC analysis (30% EtOAc/Hexanes v/v). The reaction is warmed slightly to −30° C. and acetic acid (3 L) is added slowly. Upon complete addition, water is added (0.5 L) to the reaction and the mixture is allowed to quickly warm to ambient temperature while stirring overnight. Organic solvent is removed from the reaction by distillation under reduced pressure at 45° C. To the reaction residue is added 3-4 volumes of water (6 L) and 30% hydrogen peroxide (0.7 L, 1.0 eq) slowly at ambient temperature with cooling provided to control the exotherm. The reaction is stirred for at least an hour at ambient temperature until complete as determined by TLC (15% EtOAc/Hexanes v/v). The reaction mixture is cooled to 0-5° C. and excess peroxide is quenched with the addition of 10% aqueous sodium bisulfite solution (2 L). The mixture is tested to ensure a negative peroxide result and the reaction is acidified by the addition of 6N HCl (aq) (1.2 L). The reaction is stirred until the hydrolysis reaction is complete as determined by TLC or NMR analysis. The resulting solids are collected by suction filtration to afford intermediate (13) as a yellow solid (1.0 Kg, 79%).

Intermediate (14): A reactor is charged with intermediate (13) (0.53 Kg, 3.0 mol, 1.0 eq) and dissolved in dry toluene (2.7 Kg, 3.1 L). To this solution is added dimethylsulfate (0.49 Kg, 3.9 mol, 1.30 eq) followed by solid potassium carbonate (0.58 Kg, 4.2 mol, 1.4 eq). The reaction mixture is heated to reflux and held for at least 1 hour until complete as determined by HPLC. During this time, vigorous gas evolution is observed. The reaction is then cooled to ambient temperature and diluted with distilled water (3.2 L) along with 30% NaOH (aq) (0.13 Kg, 0.33 eq). The aqueous phase is separated and the remaining toluene phase is extracted twice more with distilled water (3.2 L) combined with 30% NaOH (aq) (0.13 Kg, 0.33 eq), removing the aqueous phase each time. The organic upper phase is concentrated by distillation in vacuo (<100 mbar) at approximately 40° C. until a concentrated toluene solution is achieved. The resulting solution is cooled to ambient temperature, checked for quality and yield by HPLC, and carried forward to the next step in the synthesis without further purification (theoretical yield for intermediate (14) assumed, 0.56 Kg).

Intermediate (15a,b): A reactor is charged with 1.8 Kg (2.1 L) anhydrous toluene along with sodium hydride (0.26 Kg, 6.6 mol, 2.20 eq) as a 60 wt. % dispersion in mineral oil. To this mixture is added (0.85 Kg, 7.2 mol, 2.4 eq) diethylcarbonate as the reaction mixture is heated to 90° C. over 1 hour. A solution of intermediate (14) (~1.0 eq) in toluene from the previous step is added to the reaction while maintaining a temperature of 90° C.±5° C. Gas evolution can be observed during this addition. After complete addition, the reaction is stirred for at least 30 minutes or until complete as determined by HPLC analysis. Upon completion, the mixture is cooled to ambient temperature and diluted with 10 wt. % aqueous sulfuric acid (3.8 Kg, 3.9 mol, 1.3 eq) with agitation. The phases are allowed to separate and the lower aqueous phase is removed. The remaining organic phase is concentrated in vacuo (<100 mbar) at approximately 40° C. until a concentrated toluene solution is achieved. The resulting solution is cooled to ambient temperature and carried forward to the next step in the synthesis without further purification (theoretical yield for intermediate (15a,b) assumed, 0.85 Kg).

Intermediate (16a,b; 17a,b): A reactor is charged with a solution of intermediate (15a,b) (0.85 Kg, ~3.0 mol, ~1.0 eq) in toluene from the previous step. To the reactor is then added dimethylformamide-dimethylacetal (0.54 Kg, 4.5 mol, 1.5 eq) and the resulting solution is heated to reflux temperature (~95-105° C.). The lower boiling solvent (methanol from reaction) is allowed to distill off while the temperature is maintained at ≧90° C. Heating is continued for at least 1 hour or until complete as determined by HPLC analysis. Upon completion, the reaction containing the mixture of intermediate (16a,b), is cooled to ambient temperature and toluene (1.8 Kg, 2.1 L) along with cyclopropylamine (0.21 Kg, 3.6 mol, 1.2 eq) are added to the reaction. The reaction is stirred at ambient temperature for at least 30 minutes until complete as determined by HPLC. Upon completion, the reaction is diluted with 10 wt. % aqueous sulfuric acid (2.9 Kg, 3.0 mol, 1.0 eq) with agitation, and the phases are then allowed to separate. The aqueous phase is removed and the organic phase is concentrated under reduced pressure (<100 mbar) at approximately 40° C. by distillation. When the desired concentration is achieved, the solution is cooled to ambient temperature and the toluene solution containing the mixture of intermediate (17a,b) is carried forward to the next step in the synthesis without further purification (theoretical yield for intermediate (17a,b) assumed, ~1.1 Kg).

Intermediate (18): A reactor is charged with a solution of the mixture of intermediate (17a,b) (~4.7 Kg, ~3.0 mol) at ambient temperature. To the reactor is added N,O-bis(trimethylsilyl)acetamide (0.61 Kg, 3.0 mol, 1.0 eq) and the reaction is heated to reflux temperature (~105-115° C.) for at least 30 minutes or until complete as determined by HPLC analysis. If not complete, an additional amount of N,O-bis(trimethylsilyl)acetamide (0.18 Kg, 0.9 mol, 0.3 eq) is added to the reaction to achieve completion. Upon completion, the reaction is cooled to below 40° C. and organic solvent is removed under reduced pressure (<100 mbar) at approximately 40° C. by distillation until a precipitate is formed. The reaction is cooled to ambient temperature and the precipitated solids are isolated by suction filtration and washed with distilled water twice (1×1.8 L, 1×0.9 L). The solid is dried to afford intermediate (18) as a white solid (0.76 Kg, 82%). The material is used without further purification in the next reaction step.

Intermediate (19): A reactor is charged with solid intermediate (18) (0.76 Kg, ~2.5 mol, ~1.0 eq) at ambient temperature followed by ethanol (5.3 Kg, 6.8 L) and 32 wt. % aqueous hydrochloric acid (1.1 Kg, 10 mol). The reaction mixture is brought to reflux temperature (76-80° C.) during which time the mixture first becomes homogeneous and later becomes heterogeneous. The mixture is heated at reflux for at least 5 hours or until complete as determined by TLC analysis (15% EtOAc/Hexanes v/v). Upon completion, the reaction is cooled to 0° C.±5° C. and the precipitated solid is isolated by filtration and washed with distilled water (1.7 Kg) followed by ethanol (1.7 Kg). The isolated solid is dried to afford intermediate (19) as a white solid (0.65 Kg, ~95%). $^1$H NMR (CDCl$_3$, 300 MHz) δ (ppm): 14.58 (s, 1H), 8.9 (s, 1H), 8.25 (m, 1H), 7.35 (m, 1H), 4.35 (m, 1H), 4.08 (s, 3H), 1.3 (m, 2H), 1.1 (m, 2H). $^{19}$F NMR (CDCl$_3$+CFCl$_3$, 292 MHz) δ (ppm): –119. HPLC: 99.5% by area.

C. Synthesis of Borone Ester Chelate of 1-Cyclopropyl-7-fluoro-8-methoxy-4-oxo-1,4-dihydro-quinoline-3-carboxylic acid (20):

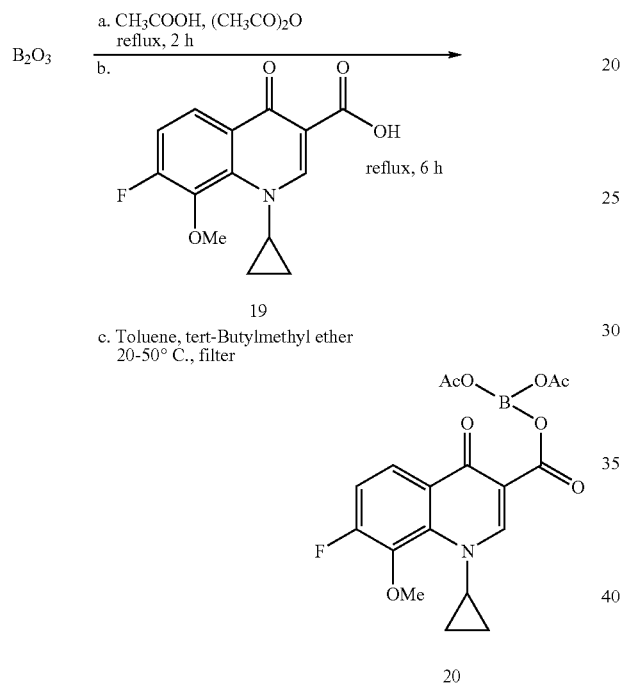

A reactor is charged with boron oxide (2.0 Kg, 29 mol) followed by dilution with glacial acetic acid (8.1 L, 142 mol) and acetic anhydride (16.2 L, 171 mol). The resulting mixture is heated to reflux temperature for at least 2 hours. The reaction contents are cooled to 40° C. and the solid 7-fluoroquinolone acid intermediate (19) (14.2 Kg, 51 mol) is added to the reaction mixture. The mixture is again heated to reflux temperature for at least 6 hours. Reaction progress is monitored by HPLC and NMR. The mixture is cooled to approximately 90° C. and toluene (45 L) is added to the reaction. The reaction is further cooled to 50° C. and tert-butylmethyl ether (19 L) is added to the reaction mixture to bring about precipitation of the product. The mixture is then cooled to 20° C. and the solid product 19 is isolated by filtration. The isolated solids are then washed with tert-butylmethyl ether (26 L) prior to drying in a vacuum oven at 40° C. (50 torr). The product yield obtained for intermediate (20) in this reaction is 86.4%. Raman (cm$^{-1}$): 3084.7, 3022.3, 2930.8, 1709.2, 1620.8, 1548.5, 1468.0, 1397.7, 1368.3, 1338.5, 1201.5, 955.3, 653.9, 580.7, 552.8, 384.0, 305.8. NMR (CDCl$_3$, 300 MHz) δ (ppm): 9.22 (s, 1H), 8.38-8.33 (m, 1H), 7.54 (t, J=9.8 Hz, 1H), 4.38-4.35 (m, 1H), 4.13 (s, 3H), 2.04 (s, 6H), 1.42-1.38 (m, 2H), 1.34-1.29 (m, 2H). TLC (Whatman MKC18F Silica, 60 Å, 200 µm), Mobile Phase: 1:1 (v/v) CH$_3$CN: 0.5N NaCl (aq), UV (254/366 nm) visualization; R$_f$=0.4-0.5.

D. Coupling of 1-Cyclopropyl-7-fluoro-8-methoxy-4-oxo-1,4-dihydro-quinoline-3-carboxylic acid (20) to (3S,5S)-(5-Methyl-piperidin-3-yl)-carbamic acid tert-butyl ester (8), and Synthesis of Malate Salt of (3S,5S)-7-[3-amino-5-methyl-piperidinyl]-1-cyclopropyl-1,4-dihydro-8-methoxy-4-oxo-3-quinolinecarboxylic acid (25):

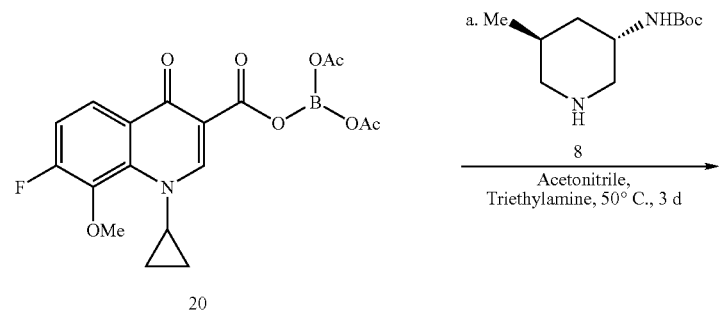

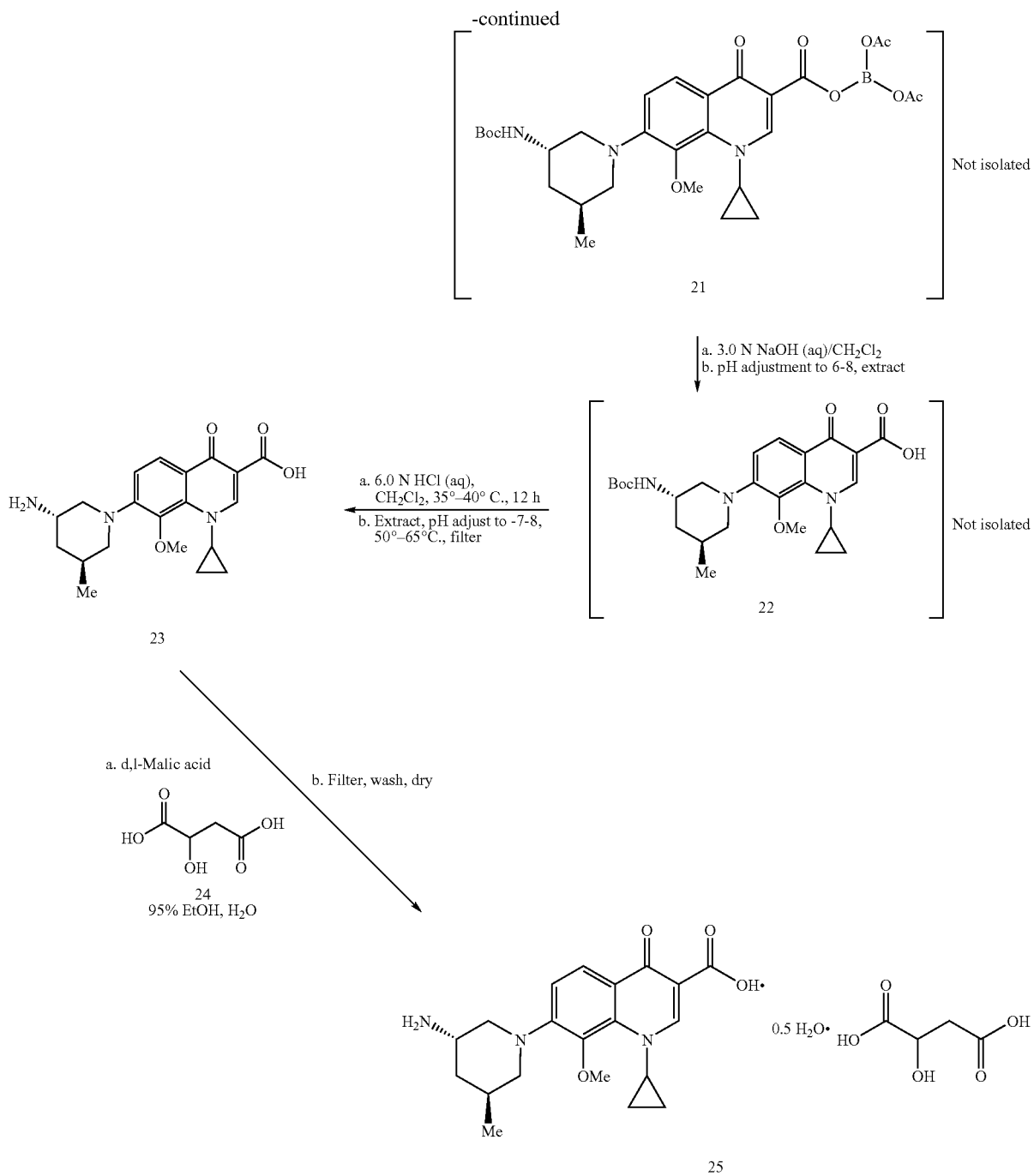

A reactor is charged with solid intermediate (20) (4.4 Kg, 10.9 mol) followed by dilution with a solution of triethylamine (TEA) (2.1 L, 14.8 mol) and piperidine side chain intermediate (8) (2.1 Kg, 9.8 mol) in acetonitrile (33.5 L, 15.7 L/Kg) at room temperature. The resulting mixture is warmed to approximately 50° C. until reaction is judged complete. Reaction progress is monitored by HPLC or reverse phase TLC. When complete, the reaction is cooled to approximately 35° C. and reaction volume is reduced to approximately half by distillation of acetonitrile under vacuum between 0-400 torr. The reactor is then charged with 28.2 Kg of 3.0N NaOH (aq) solution and the temperature is raised to approximately 40° C. Distillation under vacuum is continued between 1-4 hours or until no further distillates are observed. The reaction is then cooled to room temperature and the hydrolysis reaction is monitored by HPLC or reverse phase TLC. Upon completion, the reaction mixture is neutralized to a pH of between 6-8 by adding ~4-5 Kg of glacial acetic acid. The reactor is then charged with 12.7 Kg (9.6 L) of dichloromethane as an extraction solvent, the mixture is agitated, phases are allowed to separate, and the organic-dichloromethane phase is removed. The extraction process is repeated two additional times using 12.7 Kg (9.6 L) of dichloromethane, collecting the lower, organic phase each time. The aqueous phase is discarded and the organic extracts are combined in a single reactor. The reactor contents are heated to 40° C. and the reaction volume is reduced to approximately one half by distillation. The reactor is then charged with 20.2 Kg 6.0N HCl (aq) solution, the temperature is adjusted to 35° C., and agitation is allowed for at least 12 hours to permit the Boc deprotection reaction to occur. The reaction is monitored by HPLC or reverse phase TLC. When complete, agitation is discontinued and the phases are allowed to separate. The lower, organic phase is removed and set aside. The reactor is then charged with 12.7 Kg (9.6 L) of dichloromethane as an extraction solvent, the mixture is agitated, phases are allowed to separate, and the organic dichloromethane phase is removed. The organic extracts are combined and discarded. The remaining aqueous phase is diluted with 18.3 Kg distilled water and the temperature is raised to approximately 50° C. Distillation under vacuum (100-400 torr) is performed to remove residual dichloromethane from the reaction. The pH of the reaction is then adjusted to between 7.8-8.1 using about 9.42 Kg of 3.0N NaOH (aq) solution while keeping the temperature of the reaction below 65° C. The reaction is cooled to 50° C. and the precipitated solids are aged for at least an hour prior to cooling the mixture to room temperature. The solids are isolated by suction filtration and washed twice with 5.2 Kg portions of distilled water. The solids are dried for at least 12 hours with suction and then for an additional 12 hours in a convection oven at 55° C. The yield achieved for intermediate (23) in this example is 3.2 Kg (79%). A reactor is charged with 3.2 Kg solid intermediate (23) and the solids are suspended in 25.6 Kg of 95% ethanol as solvent. To the reactor is then added 1.1 Kg of solid D,L-malic acid (24), and the mixture is heated to reflux temperature (~80° C.). Distilled water (~5.7 L) is added to the reaction until a complete solution is achieved and 0.2 Kg of activated charcoal is added. The reaction mixture is passed through a filter to achieve clarification, cooled to 45° C. and held for a period of at least 2 hours to allow crystallization to occur. The reaction mixture is further cooled to 5° C. and the suspended solids are isolated by suction filtration. The solids are then washed with 6.6 KG of 95% ethanol and dried for at least 4 hours with suction under vacuum. The solids are then further dried in a convection oven for at least 12 hours at 45° C. to afford 3.1 Kg of intermediate (24) (70%). NMR ($D_2O$, 300 MHz) δ (ppm): 8.54 (s, 1H), 7.37 (d, J=9.0 Hz, 1H), 7.05 (d, J=9.0 Hz, 1H), 4.23-4.18 (m, 1H), 4.10-3.89 (m, 1H), 3.66 (br s, 1H), 3.58 (s, 3H), 3.45 (d, J=9.0 Hz, 1H), 3.34 (d, J=9.3 Hz, 1H), 3.16 (d, J=12.9 Hz, 1H), 2.65 (dd, J=16.1, 4.1 Hz, 1H), 2.64-2.53 (m, 1H), 2.46 (dd, J=16.1, 8.0 Hz, 1H), 2.06 (br s, 1H), 1.87 (d, J=14.4 Hz, 1H), 1.58-1.45 (m, 1H), 1.15-0.95 (m, 2H), 0.91 (d, J=6.3 Hz, 3H), 0.85-0.78 (m, 2H). TLC (Whatman MKC18F Silica, 60 Å, 200 µm), Mobile Phase: 1:1 (v/v) $CH_3CN$: 0.5N NaCl (aq), UV (254/366 nm) visualization. HPLC: Mobile Phase $H_2O$ with 0.1% formic acid/Acetonitrile with 0.1% formic acid, gradient elution with 88% $H_2O$/formic acid to 20% $H_2O$/formic acid, Zorbax SB-C8 4.6 mm×150 mm column, Part No. 883975.906, 1.5 ml/min rate, 20 min run time, 292 nm, Detector Model G1314A, S/N JP72003849, Quat Pump Model G1311A, S/N US72102299, Auto Sampler Model G1313A, S/N DE14918139, Degasser Model G1322A, S/N JP73007229; approximate retention time for intermediate (19): 13.0 min; approximate retention time for intermediate (20): 11.6 min; approximate retention time for intermediate (21): 16.3 min; approximate retention time for intermediate (22): 18.2 min; approximate retention time for intermediate (23): 8.6 min; approximate retention time for compound (25): 8.6 min.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A process for preparing a quinolone intermediate having the formula:

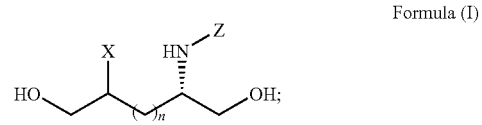

Formula (I)

wherein:
n is 1 or 2;
X is selected from the group consisting of $C_1$-$C_4$ alkyl, $C_6$-$C_{10}$ aryl or alkylaryl, and $C_3$-$C_6$ cycloalkyl; and
Z is selected from the group consisting of $CO_2X$ and COX, wherein X is as defined above;
said process comprising the steps of:
(a) reacting the compound of Formula (II):

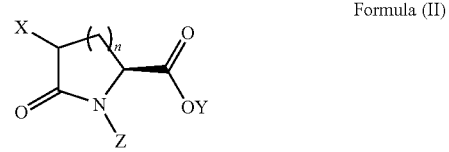

Formula (II)

wherein Y is selected from the group consisting of $C_1$-$C_4$ alkyl, $C_6$-$C_{10}$ aryl or alkylaryl, and $C_3$-$C_6$ cycloalkyl; and X, and Z are as defined for Formula (I); with about 2 to about 4 equivalents of sodium borohydride in alkanol or an admixture of alkanol/ether in a v/v ratio of from about 100/0 to about 20/80, at about −20° C. to about 10° C.;
(b) setting the temperature of the reaction mixture to a temperature in the range from about 5° C. to about 15° C.; and
(c) adding about 1.5 to about 3.0 equivalents of a calcium salt.

2. A process according to claim 1, wherein the alkanol is a $C_1$ to $C_4$ alkanol.

3. A process according to claim 1, wherein the ether is a $C_2$ to $C_6$ ether.

4. A process according to claim 2, wherein the ether is a $C_2$ to $C_6$ ether.

5. A process according to claim 1, wherein X is $C_1$-$C_4$ alkyl.

6. A process according to claim 5, wherein X is methyl.

7. A process according to claim 1, wherein Z is tert-butoxycarbonyl.

8. A process according to claim 5, wherein Y is methyl.

9. A process according to claim 1, wherein the calcium salt is selected from the group consisting of calcium chloride and calcium bromide.

10. A process according to claim 9, wherein the calcium salt is calcium chloride.

11. A process according to claim 1, wherein the compound of Formula (II) is (2S,4S)-1-(1,1-dimethylethyl)-4-methyl-5-oxo-1,2-pyrrolidinedicarboxylic acid-2-methyl ester.

12. A process according to claim 1, wherein the compound of Formula (II) is (2S,4R)-1-(1,1-dimethylethyl)-4-methyl-5-oxo-1,2-pyrrolidinedicarboxylic acid-2-methyl ester.

13. A process according to claim 1, wherein the compound of Formula (I) is (1S,3S)-(4-Hydroxyl-1-hydroxymethyl-3-methyl-butyl)-carbamic acid tert-butyl ester:

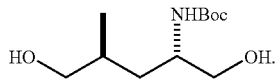

14. A process according to claim 1, wherein the compound of Formula (I) is (1S,3R)-(4-Hydroxyl-1-hydroxymethyl-3-methyl-butyl)-carbamic acid tert-butyl ester:

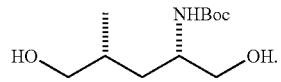

15. A process according to claim 1, wherein the alkanol solvent is selected from the group consisting of methanol, ethanol, propanol, isopropanol, and butanol.

16. A process according to claim 15, wherein the alkanol solvent is ethanol.

17. A process according to claim 1, wherein the ether solvent is selected from the group consisting of methyl tert-butyl ether (MTBE), ethylene glycol dimethyl ether, diethyl ether, tetrahydrofuran, diisopropyl ether, and dioxane.

18. A process according to claim 17, wherein the ether solvent is methyl tert-butyl ether.

19. A process according to claim 16, wherein the ether solvent is methyl tert-butyl ether.

20. A process according to claim 19, wherein the solvent ratio (v/v) of ethanol to methyl tert-butyl ether is about 1:2.

* * * * *